(12) United States Patent
Hempel

(10) Patent No.: US 8,483,797 B2
(45) Date of Patent: Jul. 9, 2013

(54) MEDICAL DIAGNOSIS OR THERAPY APPARATUS WITH AN ELECTROCHROMIC DISPLAY FOR THE PATIENT

(75) Inventor: Eckhard Hempel, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 1768 days.

(21) Appl. No.: 11/745,508

(22) Filed: May 8, 2007

(65) Prior Publication Data
US 2008/0009696 A1 Jan. 10, 2008

(30) Foreign Application Priority Data

May 8, 2006 (DE) .......................... 10 2006 021 355

(51) Int. Cl.
*A61B 5/05* (2006.01)
(52) U.S. Cl.
USPC ............ 600/418; 600/425; 600/427; 348/817
(58) Field of Classification Search
USPC .......... 600/407, 410, 411, 415, 418; 348/817; 349/33–55; 359/265–277
See application file for complete search history.

(56) References Cited

U.S. PATENT DOCUMENTS

| 4,210,015 A | | 7/1980 | Euzen et al. |
| 5,627,902 A | * | 5/1997 | Ziarati ........................... 381/385 |
| 5,959,762 A | * | 9/1999 | Bandettini et al. ............ 359/265 |

FOREIGN PATENT DOCUMENTS

| DE | 199 20 942 A1 | 11/2000 |
| DE | 102 37 924 A1 | 3/2004 |
| DE | 10 2004 007 427 A1 | 9/2005 |

OTHER PUBLICATIONS

Machine translation of DE 10237924 (original document published Mar. 2004; translation generated on Jul. 27, 2011).*

* cited by examiner

*Primary Examiner* — Parikha Mehta
(74) *Attorney, Agent, or Firm* — Schiff Hardin LLP

(57) ABSTRACT

To improve patient comfort and reduce claustrophobia experienced by patients in a medical diagnosis or therapy apparatus, in particular a CT apparatus or an MR apparatus, with an examination region demarcated by said inner wall, in which examination region a patient can be positioned, a display is arranged in a region forming at least a portion of the inner wall.

7 Claims, 1 Drawing Sheet

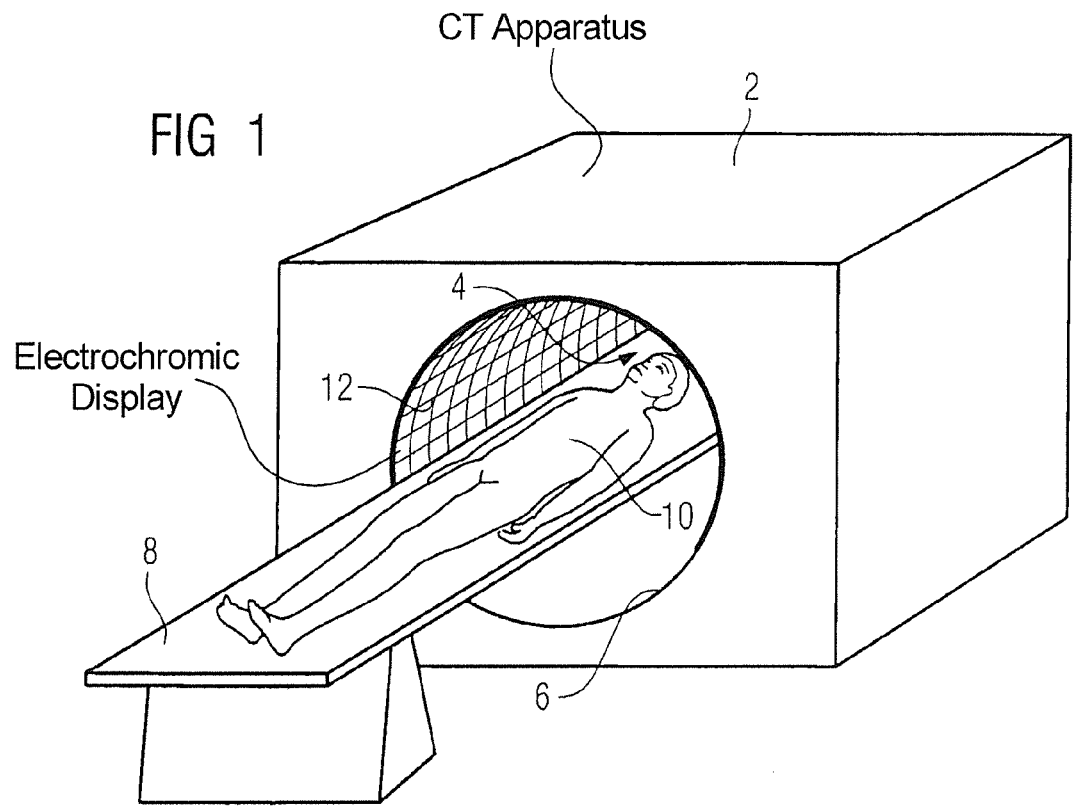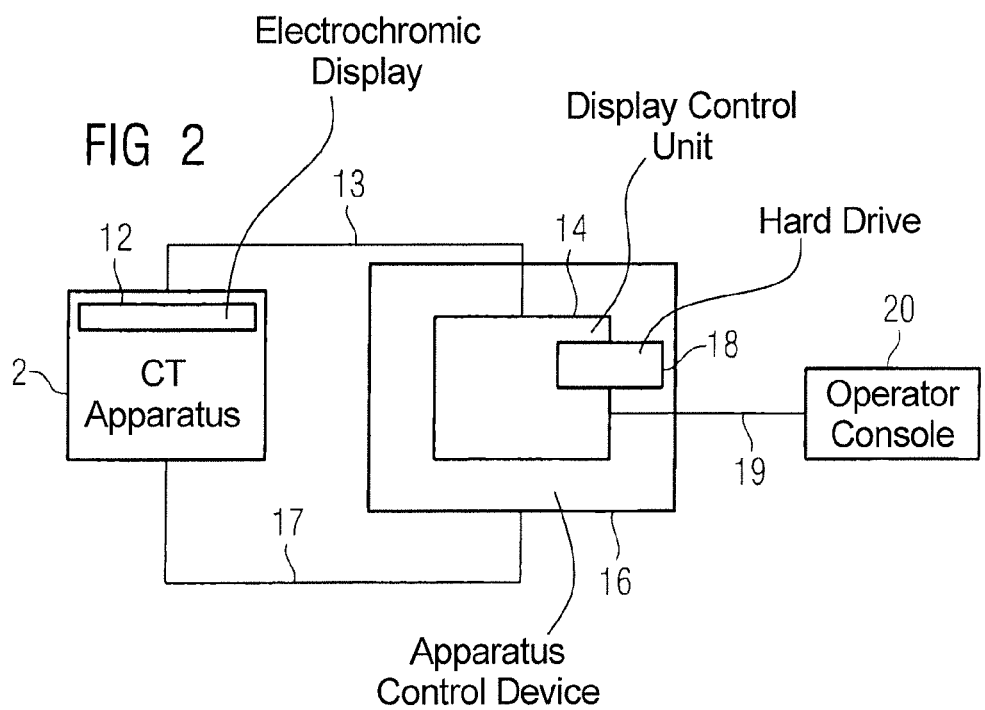

MEDICAL DIAGNOSIS OR THERAPY APPARATUS WITH AN ELECTROCHROMIC DISPLAY FOR THE PATIENT

BACKGROUND OF THE INVENTION

1. Field of the Invention

The present invention concerns a medical diagnosis or therapy apparatus (in particular a CT apparatus or an MR apparatus) of the type having an examination region demarcated by an internal wall, in which examination region a patient can be positioned. The invention furthermore concerns a method for operation of such a medical diagnosis or therapy apparatus.

2. Description of the Prior Art

A number of medical-technical apparatuses (such as, for example, CT or MR apparatuses) are characterized by their tube-shaped housing into which a patient is moved for examination or treatment. Particular patients who have a fear of enclosed spaces feel unwell when they are positioned within the tube-shaped examination region, primarily given a whole-body examination or treatment. In some patients this even leads claustrophobia, such that the examination must sometimes be terminated.

A diagnosis or therapy apparatus in which an covering element is provided in an examination/therapy region, which covering element establishes a calming atmosphere, is described in DE 10 2004 007 427 A1. The covering element (that, for example, can be formed of a pliant fiber, a cloth-like material, fur or leather) serves to optically and haptically improve the impression of the wall of the examination/therapy region, which the patient otherwise feels to be cold and technical.

In order to effectively improve the well-being of such patients who suffer anxiety in a tunnel of an MR apparatus, DE 102 37 924 Q1 discloses a display surface in the form of a projection field for image presentations, in particular for films or video sequences.

DE 199 20 942 A1 discloses with a large-surface display device, in particular for advertising and information purposes. To reduce the production costs, the display elements of the display device are fashioned as color pixels covered with a switchable electrochromic coating.

SUMMARY OF THE INVENTION

An object of the invention is to provide a great degree of patient comfort during the examination or treatment by means of a medical diagnosis or therapy apparatus.

The object is achieved in accordance with the invention by a medical diagnosis or therapy apparatus, in particular a CT apparatus or an MR apparatus, with an examination volume demarcated by an inner wall, in which examination region a patient can be positioned, wherein an electronic display made from an electrochromic material is arranged in a region forming at least a portion of the inner wall. The region is within the field of view seen by a patient when situated in the examination volume.

The basic advantage of the display is that it achieves a calming atmosphere within the examination region, such that the comfort during the examination is improved and the danger of anxiety in claustrophobic patients is reduced. An active display additionally offers the possibility to show different images during the examination of a patient. In contrast to the known covering elements, the display does not have to be exchanged each time when a new visual effect must be achieved. The display is positioned such that at least a majority of the field of view of the patient is covered. One or more images are shown over a large area that, for example, imparts vastness and extent, for example a cloudy sky, and thus have a calming effect on the patient.

The use of electrochromic materials in display devices such as micro-calculators or electron clocks is, for example, described in DE 28 54 821. Electrochromic materials are additionally frequently used as dimmable mirrors or darkenable window panes. The principle of the electrochromic display is based on the electrochromic effect that occurs in many organic materials. This causes reversible coloration of the material given an externally applied voltage. Electrochromic materials are characterized by several properties that make them particularly suitable for use as a large-surface display—they can be produced over a large area, they are very flexible and can be rolled up, they exhibit a very flat construction, a wide viewing angle and high contrast. Moreover, their manufacture is inexpensive.

In order to maximally improve the optical impression within the examination region, the entire inner wall of the examination region that is visible by the patient is preferably covered by the display. The inner wall thus acts in a particularly relaxing and comforting manner on the patient positioned in the examination region.

The display is advantageously situated directly on the inner wall of the examination region. The inner volume of the examination region is thus not unnecessarily reduced by the display.

In a preferred embodiment of the medical diagnosis or therapy apparatus, it has a control unit that controls the displace to show images and/or examination-related information. The computer-based control unit is in particular part of an overall control device for monitoring and controlling the medical diagnosis or therapy apparatus, such that the control unit also indirectly communicates with components of the apparatus that deliver their current information about the workflow of the examination. This examination-related information that is displayed to the patient comprises, for example, the remaining running time of the examination or patient instructions such as breathing commands.

The control unit appropriately has a data medium on which images are stored to be shown on the display. The data medium can be a storage medium for electronic (USB stick), magnetic (hard drive, diskette) or optical (CD, DVD) storage. Moreover, the data medium is readable only, writeable once or alternatively re-writeable. The images stored on the data medium are retrieved by the control unit and shown on the display. For example, during the examination/treatment only a single image is displayed or, alternatively, a series of images is determined that are alternately played back in the manner of a screen saver.

When patient instructions are shown on the display, it is of great importance that the instructions can be updated at any time dependent on the workflow of the examination and reactions of the patient. It is therefore particularly advantageous for the control unit to be connected with an operator console to set (adjust) the images and/or information shown on the display. At any time the operating personnel of the apparatus can thereby change and update the images and information shown on the display corresponding to the examination workflow. However, the speed with which the images are shown or their sequence during the examination and also be changed simply via the operating console.

The object is furthermore inventively achieved by a method for operation of a medical diagnosis or therapy apparatus, in particular of a CT apparatus or an MR apparatus, with an examination region demarcated by an inner wall, in which examination region a patient can be positioned, whereby images and/or examination-related information is shown with the aid of a display mounted on the inner wall.

The advantages and preferred embodiments listed with regard to the medical diagnosis or therapy apparatus are reasonably to be carried over to the method.

DESCRIPTION OF THE DRAWINGS

FIG. 1 is a perspective view of a CT apparatus with a display arranged on an inner wall.

FIG. 2 is a schematic illustration of a CT apparatus with an overall control device associated with the CT apparatus.

DESCRIPTION OF THE PREFERRED EMBODIMENTS

In FIG. 1 a CT apparatus 2 is shown as an example for a medical diagnosis or therapy apparatus that has a tube-like examination volume 4 that is bounded by an inner wall. The medical diagnosis or therapy apparatus can likewise be an MR apparatus or a treatment apparatus in which the patient treatment occurs in a narrow space. The inner wall 6, like that of conventional CT apparatuses, exhibits a smooth surface made from plastic. A horizontally movable patient bed 8 with a patient 10 situated thereupon is moved into the examination volume 4.

A display 12 that, in this exemplary embodiment, covers the entire field of view of the patient 10 is arranged directly situated on the inner wall 6. The display 12 comprises an electrochromic material that exhibits a low thickness and is adapted to the shape of the inner wall 6, such that the display 12 occupies as little space as possible in the examination volume 4.

The display 12 is controlled via a control line 13 from a display control unit 14 that is shown in FIG. 2. Both images and examination-relevant information such as, for instance, the remaining duration of the examination or patient instructions for breath control ("Breathe", "Do not breathe") are thereby shown on the display 12. In this exemplary embodiment the display control unit 14 is part of an overall control device 16 that controls the CT apparatus 2 via a control line 17. The display 12 thus can be controlled particularly easily dependent on the workflow of the examination. The display control unit 14 alternatively can be connected with the overall control device 16 in terms of data without it physically being a part of the overall control device 16. The control unit 12 can also function separate from the overall control device 16 without the two communicating and exchanging data with one another.

In this exemplary embodiment the control device 12 moreover has a hard drive 18, representing a medium on which images are stored in a suitable format to be shown on the display 12, or a source via which such images are accessible. The control unit 12 and the overall control device 16 hereby jointly utilize the hard drive 18. Instead of the hard drive 18, another peripheral device such as, for example, a DVD-ROM drive, CD-ROM drive or disk drive or a USB port can be provided with which the images are read from an exchangeable data medium (DVD, CD, diskette) or from a USB stick.

The sequence of images and information that are shown on the display 12 during the examination as well as their display duration can be set once by means of a suitable software program and then permitted to run. However, in this exemplary embodiment the control unit 12 is connected via a further line 19 with an operator console 20 allowing the operating personnel to alter the settings of the display 12 at any time. This also enables a communication between the operating personnel and the examined patient 10 by the updated instructions to the patient 10 being shown on the display 12 dependent on the examination workflow.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical diagnosis or therapy apparatus comprising:
   a patient-receiving unit comprising an examination volume configured to receive a patient therein, said examination region being demarcated by an inner wall having a tubular shape that defines a tubular opening in which said examination volume is located; and
   a display disposed in a region forming at least a portion of said inner wall, said region being within a field of view seen by a patient when situated in said examination volume, said display being comprised of an electrochromic material and having a curved shape conforming to said tubular shape of said inner wall.

2. A medical diagnosis or therapy apparatus as claimed in claim 1 wherein said region encompasses an entirety of said field of view seen by the patient, and wherein said display is co-extensive with said region.

3. A medical diagnosis or therapy apparatus as claimed in claim 1 wherein said display is situated directly on said inner wall.

4. A medical diagnosis or therapy apparatus as claimed in claim 1 comprising a control unit connected to said display, said control unit controlling a content displayed at said display, selected from the group consisting of images and information relevant to an examination of the patient.

5. A medical diagnosis or therapy apparatus as claimed in claim 4 wherein said control unit comprises a data storage medium on which images are stored to be shown on said display.

6. A medical diagnosis or therapy apparatus as claimed in claim 5 comprising an operator input unit connected to said control unit allowing manual entry of said content.

7. A medical diagnosis or therapy apparatus as claimed in claim 1 wherein said patient-receiving unit is selected from the group consisting of computed tomography data acquisition units and magnetic resonance data acquisition units.

* * * * *